(12) United States Patent
Chauchard et al.

(10) Patent No.: US 8,730,467 B2
(45) Date of Patent: May 20, 2014

(54) SPECTROSCOPIC PROBE AND METHOD FOR DETECTING AN INHOMOGENEITY

(75) Inventors: Fabien Chauchard, Prades le Lez (FR); Sylvie Roussel, Prades le Lez (FR)

(73) Assignee: Indatech, Prades le Lez (FR)

( * ) Notice: Subject to any disclaimer, the term of this patent is extended or adjusted under 35 U.S.C. 154(b) by 677 days.

(21) Appl. No.: 12/695,718

(22) Filed: Jan. 28, 2010

(65) Prior Publication Data

US 2010/0302538 A1 Dec. 2, 2010

Related U.S. Application Data

(63) Continuation-in-part of application No. 12/695,551, filed on Jan. 28, 2010.

(30) Foreign Application Priority Data

May 28, 2009 (FR) ...................................... 09 53521
Jan. 21, 2010 (FR) ...................................... 10 50379

(51) Int. Cl.
*G01N 21/00* (2006.01)

(52) U.S. Cl.
USPC .......................................... 356/300; 385/115

(58) Field of Classification Search
CPC .. A61B 1/07; A61B 1/00165; A61B 1/00167; G02B 6/04; G01N 21/474; G01N 21/4742; G01N 21/4745; G01N 21/4447

USPC ............................ 356/300; 385/117; 600/182
See application file for complete search history.

(56) References Cited

U.S. PATENT DOCUMENTS

| | | | | |
|---|---|---|---|---|
| 4,573,761 | A * | 3/1986 | McLachlan et al. | 385/115 |
| 6,678,541 | B1 * | 1/2004 | Durkin et al. | 600/310 |
| 7,440,659 | B2 * | 10/2008 | Liu et al. | 385/39 |
| 2003/0191398 | A1 * | 10/2003 | Motz et al. | 600/478 |

* cited by examiner

*Primary Examiner* — Kara E Geisel
(74) *Attorney, Agent, or Firm* — Nath, Goldberg & Meyer; Jerald L. Meyer

(57) ABSTRACT

A method for detecting by spectroscopy an inhomogeneity (I) in a sample (E), includes that (i) the sample (E) is illuminated with incident light using means (23) for illuminating the sample (E), and (ii) the light re-emitted by the sample (E) is collected using means (24; 24') for collecting the light, wherein (i) the light re-emitted by the sample (E) is collected at different spots arranged each spaced apart from the other spots and being located at the same distance from the means (23) for illuminating this sample (E) or their barycenter, and (ii) the presence of an inhomogeneity (I) in the sample (E) is determined based on the signals corresponding to the light re-emitted and collected at least at two different spots. A spectroscopic probe (2) and a device for analyzing a sample by spectroscopy implementing the method are also disclosed.

23 Claims, 2 Drawing Sheets

SPECTROSCOPIC PROBE AND METHOD FOR DETECTING AN INHOMOGENEITY

BACKGROUND OF THE INVENTION (1) Field of the Invention

The present invention relates to a spectroscopic device for analyzing a sample by spectroscopy. This invention also relates to a method for detecting, by spectroscopy, an inhomogeneity in a sample as well as a method for determining, also by spectroscopy, the absorption and/or diffusion coefficient of such a sample, in particular implementing such a probe.

This invention is related to the field of the manufacture of the devices allowing carrying out an analysis of a sample by spectroscopy.

In this respect, it should be noted that spectroscopy is a technique largely implemented in industry and research when both solid and liquid samples should be analyzed.

(2) Description of the Prior Art

In fact, various types of spectroscopy are known, each of these types corresponding substantially to a range of wavelengths of the light emitted (UV, visible, infrared, near infrared, mid infrared, Raman), and allowing to characterize in particular some of these samples and/or to determine some characteristics of such a sample.

In particular, it is known to implement a spectroscopy technique for characterizing products formed, by way of non-restrictive examples, by pharmaceutical tablets, gels, emulsions, powders, flours, products in suspension.

More specifically, such a spectroscopy technique can then be implemented to determine the homogeneity and/or the uniformity of such a product.

In this respect, various methods allowing determining such homogeneity and/or such uniformity are known.

In particular, a first method consists in illuminating a sample at an illuminating point, and in measuring several series of spectra at a measuring point different from the illuminating point and fixed with respect to it.

In fact, this method consists, between two series of spectra, either in repositioning (manually or automatically) the sample in order to acquire spectra in different areas of this sample, or in mechanically stirring this sample (in particular using a mixer).

A first drawback of this method resides in that repositioning the sample takes a certain time. A second drawback of this method resides in that a bad repositioning of the sample induces a variation in the spectrum, which will be interpreted as an inhomogeneity, whereas it is, instead, a mere manipulation and/or positioning error.

In order to cope with these drawbacks, a new technique has been devised, which consists in submitting the sample to two measurements, one of which is in reflection, while the other one is in transmission. This technique however brings a new drawback consisting in that the spectra obtained are by no means comparable, since they correspond to lights having travelled over different distances with respect to the sample.

A second method, aiming at determining the homogeneity and/or uniformity of a product, consists in using a hyperspectral camera for acquiring a two-dimensional image of this product and comprised of a plurality of pixels.

In fact, this method consists, first, in acquiring at least one spectrum for each pixel of the image of the product and, afterwards, in analyzing and comparing to each other the spectrum or the spectra of these pixels.

This method advantageously allows analyzing the whole surface of the product and comparing spectra acquired in similar conditions (illumination of the sample, travel distances of the light with respect to this sample . . . ).

This method has a number of drawbacks. Thus, a first drawback of this method consists in that the time for acquiring the spectra is particularly long (namely in the range of several minutes), which makes it difficult to contemplate this method for continuously characterizing a product.

However, the main drawback of this method consists in that only the surface of the sample can be analyzed. Thus, this method allows by no means detecting the presence of a physical (agglomerate) or chemical (concentration of active substance) inhomogeneity located under the surface if the product and in depth in the product.

SUMMARY OF THE INVENTION

The invention aims at dealing with the drawbacks of the devices and methods of the state of the art, this through a spectroscopic probe of a new design and a new characterization method for characterizing.

To this end, the invention relates to a spectroscopic probe for a device for analyzing a sample by spectroscopy and including:
  means for illuminating the sample to be analyzed with incident light;
  means for collecting light re-emitted by the sample to be analyzed under the action of the incident light;
  a contact surface, oriented towards the sample to be analyzed, at the level or near which the means for illuminating the sample and/or the means for collecting re-emitted light are located.

This spectroscopic probe is characterized in that the means for collecting light re-emitted by the sample constitute at least one set of means for collecting re-emitted light, such a set including a plurality of these means for collecting re-emitted light arranged each spaced apart from the other ones and at the same distance from the means for illuminating the sample or their barycenter.

The invention also relates to a spectroscopic probe having the above-described features, and including means for collecting light re-emitted by the sample, which constitute a plurality of sets of means for collecting this re-emitted light, each of these sets including a plurality of these means for collecting the re-emitted light arranged each spaced apart from the other ones and at the same distance from the means for illuminating the sample or their barycenter, while the means for collecting the re-emitted light that such a set includes are located, with respect to the means for illuminating the sample or their barycenter, at a distance differing from the one at which the means for collecting the re-emitted light that another set includes are located.

According to another feature, the means for collecting light re-emitted by the sample, which a same set of these means includes, are arranged on a circle the center of which coincides with the means for illuminating the sample or their barycenter.

An additional feature consists in that the means for collecting light re-emitted by the sample, which a same set of these means includes, are regularly angularly distributed according to a circle, notably in an equiangular way, more particularly so that two means for collecting the re-emitted light, which follow each other on this circle, are angularly shifted by an angle between 30 and 180°, preferably between 36 and 120°.

The invention also relates to a method for detecting, by spectroscopy, an inhomogeneity in a sample, this method consisting in that:

the sample is illuminated with incident light, this through means for illuminating this sample with such incident light;

the light re-emitted by the sample under the action of the incident light is collected, this through means for collecting such light re-emitted by the sample.

This method is characterized in that:

the light re-emitted by the sample is collected, this at various spots arranged each spaced apart from the other ones and located at the same distance from the means for illuminating this sample or their barycenter;

on the basis of the signals corresponding to the light re-emitted and collected at least at two different spots, the presence of an inhomogeneity in the sample is determined.

Finally, the invention relates to a method for determining, by spectroscopy, the absorption and/or diffusion coefficient of a sample, this method consists in that:

the sample is illuminated with incident light, this through means for illuminating this sample with such incident light;

the light re-emitted by the sample under the action of the incident light is collected, this through means for collecting such light re-emitted by the sample.

This method is characterized in that:

the light re-emitted by the sample is collected, this at least at two different spots each located at a different distance from the means for illuminating this sample or their barycenter;

on basis of the signals corresponding to the light re-emitted and collected at these different spots, the absorption and/or diffusion coefficient of the sample is determined.

The probe according to the invention includes means for collecting light re-emitted by the sample, which constitute at least one set of these means including a plurality of these means arranged each spaced apart from the other ones and at the same distance from the means for illuminating the sample or their barycenter.

The means for collecting light re-emitted by the sample, which a same set of these means includes, are advantageously arranged on a circle the center of which coincides with the means for illuminating the sample or their barycenter.

Such an embodiment advantageously makes it possible to collect the light backscattered by the sample at a same distance from the light source, but at different points (spaced apart from each other) of the sample, this under the same conditions of analysis (same incident light, same wavelength, same position of the probe with respect to the sample . . . ), in one single operation and without having to move or reposition this sample or the probe.

Another feature consists in that the light emitted towards the sample not only is re-emitted by the surface of the sample, but also penetrates into this sample before being re-emitted. This advantageously makes it possible to detect an inhomogeneity and/or a lack of uniformity both at the surface of the sample and inside it.

Further goals and advantages of this invention will become clear during the following description referring to embodiments that are given only by way of indicative and non-restrictive examples.

BRIEF DESCRIPTION OF THE DRAWINGS

This description will be better understood when referring to the attached drawings, in which.

DETAILED DESCRIPTION OF THE PREFERRED EMBODIMENTS

Figure 1:
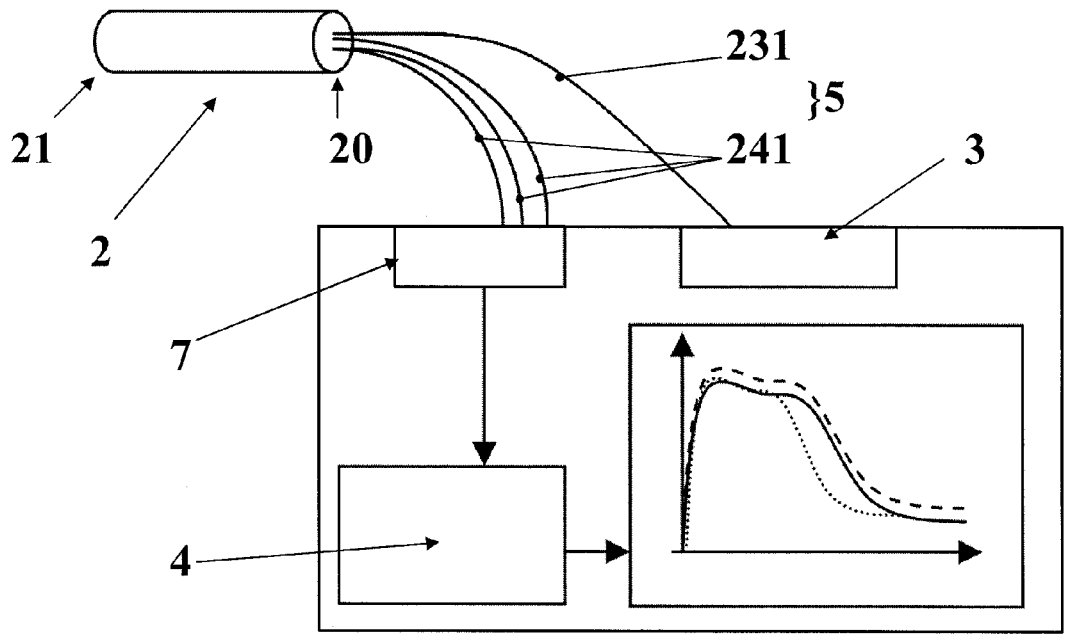
FIG. 1 is a schematic view of a device for analyzing a sample by spectroscopy, including a spectroscopic probe according to the invention.

The invention relates to the field of the manufacture of devices allowing carrying out an analysis of a sample E by spectroscopy.

In a known way, such an analysis device 1 by spectroscopy includes a spectroscopic probe 2 the features of which are described in more detail below.

This analysis device 1 also includes means 3 for emitting monochromatic or polychromatic light, in particular within a range of ultraviolet, visible, infrared, near infrared or also mid infrared wavelengths. This emitted light will be used for illuminating the sample E to be analyzed, in particular by means of the above-mentioned spectroscopic probe 2.

In addition, the analysis device 1 includes means 4 for measuring and/or processing at least one optical signal re-emitted by the sample E, in particular under the action of the illumination of this sample E by the above mentioned light.

In addition, the analysis device 1 includes means 5 for connecting, to the spectroscopic probe 2, said means 3 for emitting monochromatic or polychromatic light and/or said means 4 for measuring and/or processing at least one re-emitted optical signal.

In a known way, this means 3 for emitting monochromatic or polychromatic light as well as the means 4 for measuring and/or processing an optical signal can be integrated within an ultraviolet, visible, infrared, near infrared, mid infrared or Raman spectrometer.

The invention relates, in particular, to a spectroscopic probe 2, which adopts a shape and dimensions that allow, as the case may be, an easy grip by an operator entrusted with the analysis of the sample E, or its mounting onto a support that an installation for analyzing, producing or conveying such a sample E includes.

In particular, such a probe 2 can adopt the shape of a tube having a preferably circular cross-section, a length ranging from 100 to 800 mm (preferably in the range of about 200 to 600 mm), and an outer diameter ranging from 5 mm to 35 mm (preferably in the range of about 15 mm).

This probe 2 includes, firstly, a first end 20 at the level of which this probe 2 is connected to the means 3 for emitting monochromatic or polychromatic light as well as to the means 4 for measuring and/or processing a re-emitted optical signal, this through the connecting means 5, and, secondly, a second end 21 (referred to as free end) provided with a contact surface 22, aimed at being oriented towards the sample E to be analyzed, and through which this probe 2 cooperates with this sample E.

Figure 3:
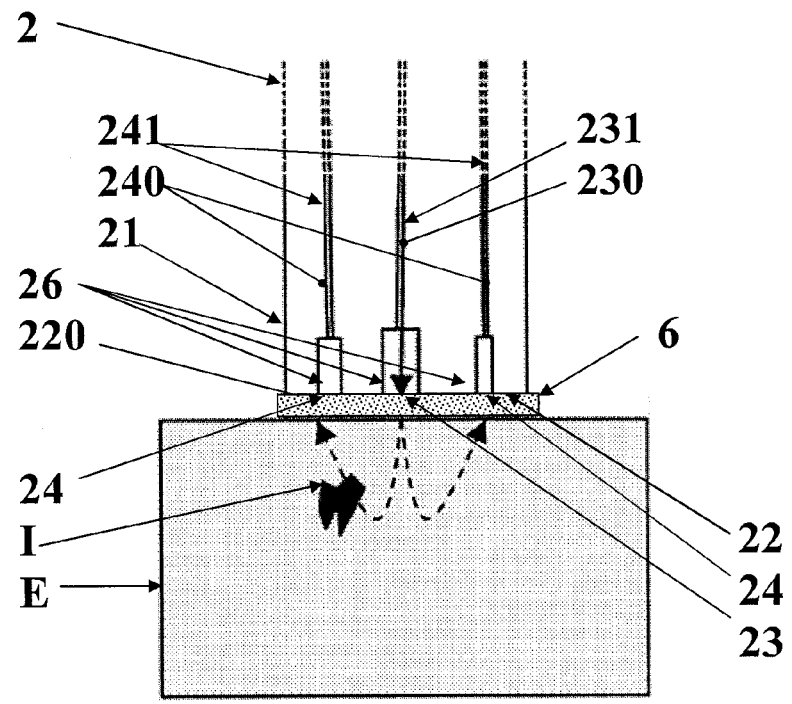
FIG. 3 is a schematic view of the probe shown in FIG. 2 and into contact with the surface of a sample to be analyzed and containing an inhomogeneity.

In this respect, it should be noted that the contact surface 22 of this probe 2 can cooperate directly with this sample E, in particular through direct contact between this contact surface 22 and this sample E, as shown in FIG. 3.

However, this contact surface 22 can also cooperate indirectly with this sample E, in particular through an intermediate element interposed between this contact surface 22 and this sample E. Such an intermediate element can consist of a measuring window (made of glass, quartz, sapphire or the like) at the front of which this contact surface 22 is positioned, at the rear of which the sample E is located, and, also, that notably a unit for transporting or manufacturing this sample E includes.

Such an intermediate element can also consist of a diffusing element 6, as it will be described below.

Another feature of this contact surface 22 consists in that it extends in a direction forming a determined angle with the general direction of extension of the probe 2 (in particular with respect to the axis of the tube this probe 2 includes).

According to a first embodiment, not shown, this contact surface 22 extends in a direction forming an angle ranging from 35 to 55° (preferably) 45° with respect to the direction of the axis of the tube.

However and as can be seen in FIGS. 1 and 3, this contact surface 22 preferably extends substantially perpendicularly to the axis of this tube.

Another feature of this spectroscopy probe 2 consists in that it includes, firstly, means 23 for illuminating the sample E to be analyzed with an incident light, in this case, the light emitted by the above-mentioned means 3 for emitting monochromatic or polychromatic light (in particular within a range of ultraviolet, visible, infrared, near infrared or also mid infrared wavelengths) and, secondly, means (24; 24') for collecting light (here too monochromatic or polychromatic light, in particular within a range of ultraviolet, visible, infrared, near infrared or also mid infrared wavelengths) re-emitted by the sample E to be analyzed under the action of the incident light.

In fact, these means 23 for illuminating the sample E and/or these means (24; 24') for collecting the light re-emitted by this sample E are located nearby the contact surface 22 (notably set back with respect to this contact surface 22) or, preferably, at the level of this contact surface 22 (notably flush with this contact surface 22).

According to the invention, the means (24; 24') for collecting the light re-emitted by the sample E constitute at least one set (25; 25') of means (24; 24') for collecting this re-emitted light. Such a set (25; 25') includes a plurality of these means (24a, 24b, 24c; 24'a, 24'b, 24'c) for collecting the re-emitted light arranged each spaced apart from the other ones, and at the same distance (d; d') from the means 23 for illuminating the sample E or the barycenter of these means 23 for illuminating the sample E.

Figure 2:
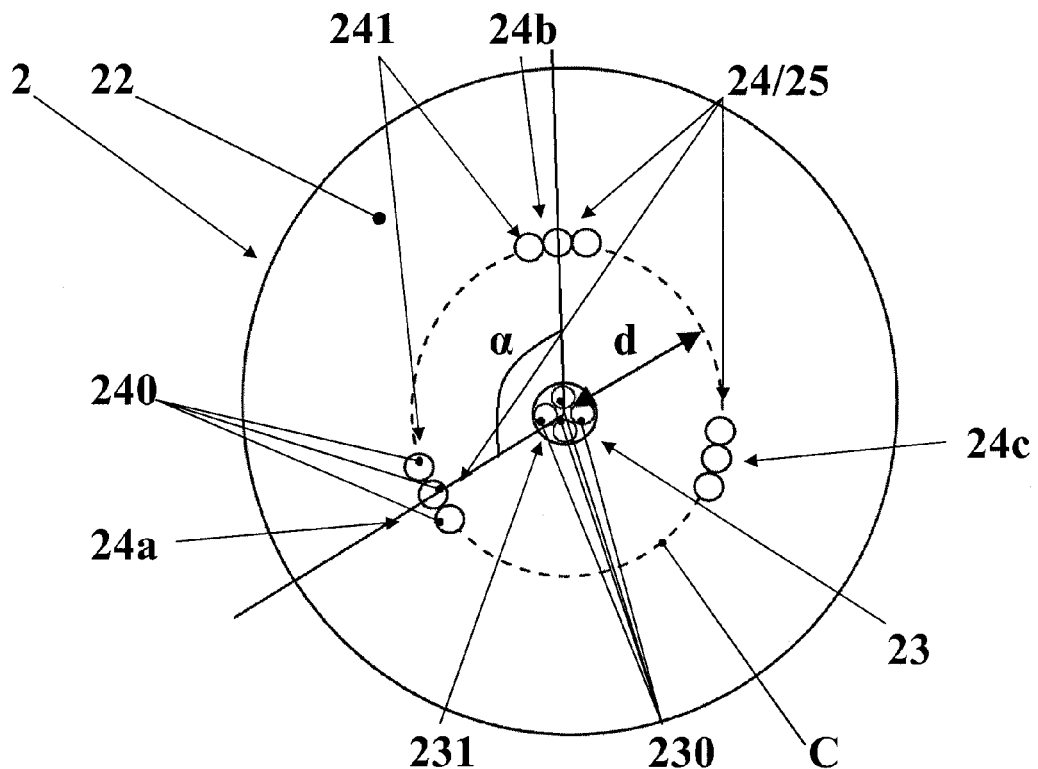
FIG. 2 is a schematic front view of the free end of the probe shown in FIG. 1 and corresponding to a first embodiment of this probe.
Figure 4:
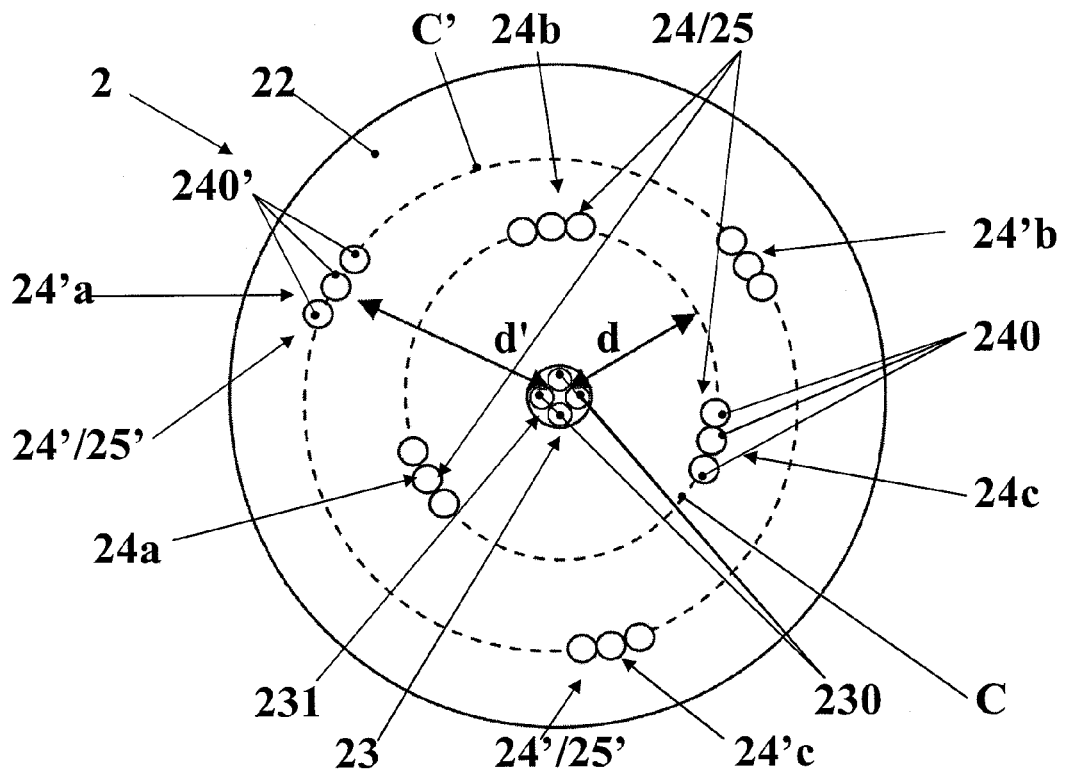
FIG. 4 is a view similar to FIG. 2 and corresponding to a second embodiment of the probe.

In fact, such a set (25; 25') of means (24; 24') for collecting the light re-emitted by the sample E includes at least two of these means (24; 24') for collecting the re-emitted light, or even (and preferably as shown in FIGS. 2 to 4) three (24a, 24b, 24c; 24'a, 24'b, 24'c) of these means (24 24') for collecting the re-emitted light.

According to a first embodiment shown in FIGS. 2 and 3, the means 24 for collecting the light re-emitted by the sample E constitute one single set 25 of means 24 for collecting this re-emitted light. Such a set 25 then includes a plurality of these means (24a, 24b, 24c) for collecting the re-emitted light arranged each spaced apart from the other ones and at the same distance d from the means 23 for illuminating the sample E or their barycenter.

However, according to another embodiment, the means (24; 24') for collecting the light re-emitted by the sample E constitute a plurality of sets (25; 25') of means (24; 24') for collecting this re-emitted light. Each of these sets (25; 25') includes a plurality of these means (24a, 24b, 24c; 24'a, 24'b, 24'c) for collecting the re-emitted light arranged each spaced apart from the other ones and at the same distance (d; d') from the means 23 for illuminating the sample E or their barycenter. In addition, the means (24; 24') for collecting the re-emitted light that such a set (25; 25') includes are located, with respect to the means 23 for illuminating the sample or their barycenter, at a distance (d; d') different from the distance (d'; d) at which are located the means (24'; 24) for collecting the light re-emitted by the sample E that another set (25'; 25) of these means (24'; 24) includes.

Each of these sets (25; 25') also includes, firstly, a plurality (24a, 24b, 24c; 24'a, 24'b, 24'c) of these means (24; 24') for collecting the re-emitted light arranged each spaced apart from the other ones and at the same distance (d; d') from the means 23 for illuminating the sample or their barycenter and, secondly, means (24; 24') for collecting the re-emitted light located at a distance (d; d') from the means 23 for illuminating the sample E or their barycenter differing from the distance (d'; d) of the means (24'; 24) for collecting the re-emitted light that another set (25'; 25) includes.

In FIG. 4 is shown a particular embodiment corresponding to a probe 2 including two sets (25; 25') of means (24; 24') for collecting the light re-emitted by the sample E and located at two different distances (d; d') from the means 23 for illuminating the sample E or their barycenter.

According to another feature of the invention, the means (24; 24') for collecting the light re-emitted by the sample E that a same set (25; 25') of these means (24; 24') includes are arranged on a circle (C; C') the center of which coinciding with the means 23 for illuminating the sample or their barycenter.

In the case of a plurality of sets (25; 25') of means (24; 24') for collecting the re-emitted light (in particular two of these sets 25; 25' as shown in FIG. 4), the means (24; 24') for collecting the re-emitted light that one set (25; 25') of these means (24; 24') includes and the means (24'; 24) for collecting the re-emitted light that another set (25'; 25) of these means (24'; 24) includes are arranged on two concentric circles (C; C') the center of which coinciding with the means (23) for illuminating the sample or their barycenter.

An additional feature of the invention consists in that the means (24; 24') for collecting the light re-emitted by the sample E that a same set (25; 25') of these means (24; 24') includes are regularly angularly distributed over the circle (C; C'), notably in an equiangular way.

In this respect, it should be noted that the means (24; 24') for collecting the light re-emitted by the sample E that a same set (25; 25') of these means (24; 24') includes are distributed according to such a circle (C; C'), this so that two means (24; 24') for collecting the re-emitted light and following each other on this circle (C; C') are angularly shifted by an angle α between 30 and 180°, preferably between 36 and 120°.

Thus, for an angle α of 180°, such a set (25; 25') includes two means (24; 24') for collecting the re-emitted light, while for an angle α of 30°, such a set (25; 25') includes 12 of them.

The probe preferably includes between 3 (preferred embodiment shown in FIGS. 2 and 4) and 10 sets (25; 25') corresponding to an angular shift of 120°, respectively 36°.

It is more particularly such an angular shift by an angle α which allows a spacing apart of each of the means (24; 24') for collecting the re-emitted light that a same set (25; 25') includes, relative to the other means (24; 24') of that same set (25; 25').

In the case of a plurality of sets (25; 25') of means (24; 24'), the means (24; 24') for collecting the re-emitted light that one set (25; 25') of these means (24; 24') includes are angularly shifted (here too, preferably regularly) with respect to the means (24'; 24) for collecting the re-emitted light that another set (25'; 25) of these means (24'; 24) includes.

It should be noted in this respect that the means (24; 24') for collecting the re-emitted light that one set (25; 25') of these means (24; 24') includes are located on the bisecting line of an angle formed by two successive means (24'a, 24'b; 24a, 24b) for collecting the re-emitted light that another set (25'; 25) of these means (24'; 24) includes and by the illuminating means 23 or their barycenter.

In other words, the means (24; 24') for collecting the re-emitted light that one set (25; 25') of these means (24; 24') includes are shifted in an equiangular way with respect to two successive means (24'; 24) for collecting the re-emitted light that another set (25'; 25) of these means (24'; 24) includes.

According to another feature of the probe 2 according to the invention, one means (24; 24') for collecting the light re-emitted by the sample E includes at least one optical fiber (240, 240') or (and preferably) a series (241; 241') of optical fibers (240; 240') formed of a plurality of optical fibers (240; 240'), more particularly of 3 optical fibers (240; 240') as shown in FIGS. 2 a 4.

When the means (24; 24') for collecting the re-emitted light includes a series (241; 241') of optical fibers (240; 240'), the optical fibers (forming such a series 241; 241' of optical fibers 240; 240') are juxtaposed and/or arranged according to an arc of a circle (in particular corresponding to the above-mentioned circle C; C') the center of which coincides with the means 23 for illuminating the sample E or their barycenter.

As mentioned above, the means (24; 24') for collecting the light re-emitted by the sample E that a same set (25; 25') of these means (24; 24') includes are arranged each spaced apart from the other ones.

In this respect, it should be noted that, according to an additional feature, the space between two means (24; 24') for collecting the light re-emitted by the sample E that a same set (25; 25') includes, and which follow each other along a same circle (C; C'), corresponds to at least the width (i.e. to the diameter of an optical fiber 240; 240') of such means (24; 24') for collecting the re-emitted light, or even (and preferably) to the length of such means (24; 24'). In fact, such a length is defined either by the diameter of an optical fiber (240; 240') when such means (24; 24') is formed of one single optical fiber (240; 240'), or by the sum of the diameters of each of the optical fibers (240; 240') that one means (24; 24') formed of a series (241; 241') of optical fibers (240; 240') includes.

According to another feature of the invention, the means 23 for illuminating the sample E include at least one optical fiber 230 or (and preferably) at least one bundle of optical fibers 231, in particular formed of at least two optical fibers 230.

It should be noted that an optical fiber (that the means 23 for illuminating the sample E and/or the means 24; 24' for collecting the light re-emitted by this sample E includes) has an end positioned either nearby the contact surface 22 of the probe 2 (namely set back with respect to this contact surface 22) or at the level of this contact surface 22 (namely flush with this contact surface 22).

The optical fiber or fibers 230 of the means 23 for illuminating the sample E have another end connected to the above-mentioned means 3 for emitting monochromatic or polychromatic light, or even to the spectrometer.

Likewise, the fibers (240; 240') of the means (24; 24') for collecting the light re-emitted by the sample E have another end connected to the means 4 for measuring and/or processing an optical signal, or even to the spectrometer.

These optical fibers (230; 240) then form the means 5 for connecting the probe 2, as the case may be, to this means 3 for emitting monochromatic or polychromatic light, and/or to these means 4 for measuring and/or processing an optical signal, or even to the spectrometer.

Another feature of the spectroscopic probe 2 consists in that its contact surface 22 includes at least one means 220 for receiving the light re-emitted by the sample E.

According to a first embodiment, this means 220 for receiving the re-emitted light is of a reflecting type and is formed of either at least one polished or white portion of this contact surface 22 or a reflecting coating that at least one portion of this contact surface 22 includes.

A particular embodiment consists in that the contact surface 22 of the probe 2 is at least partially made out of metal and the means 220 (of a reflecting type) for receiving the re-emitted light is then formed by the polished metal of this contact surface 22.

According to a second embodiment, this means 220 for receiving the re-emitted light is of an at least partly absorbent type and is formed either of a colored material forming at least one portion of this contact surface 22, or of a colored coating that at least one portion of this contact surface 22 includes.

A particular embodiment consists in that this means 220 for receiving the re-emitted light is of a fully absorbent type and is formed either of a black material (in particular an epoxy resin and graphite) entering into the composition of this contact surface 22, or of a black coating inserted, applied against or (and preferably) deposited on this contact surface 22.

An additional feature consists in that the probe 2 includes at least one through opening 26 provided for in the wall of this probe 2, in particular in the wall at the level of which the contact surface 22 of the probe 2 is defined.

In fact, such a through opening 26 ends at the level of this contact surface 22 and is intended to receive, internally, at least one means 23 for illuminating the sample E or at least one means (24, 24') for collecting the re-emitted light (in particular at least one optical fiber that such illuminating means 23 or collecting means 24 includes), the end of which is preferably positioned substantially flush with this contact surface 22.

It should be noted that, in the case of illuminating means 23 and/or collecting means (24; 24) formed of a bundle 231 or a series (241; 241') of optical fibers (230; 240; 240'), in particular positioned juxtaposed, such a through opening 26 can consist of a slit provided for in the wall of the probe 2 at the level of which the contact surface 22 is defined.

Finally, the probe 2 of the invention also includes means for protecting the means 23 for illuminating the sample and/or the means 24 for collecting light re-emitted by this sample E, or even the contact surface 22.

In fact, such means for protecting is positioned at the front of this contact surface 22 and against this contact surface 22, being more particularly inserted against this contact surface 22.

According to a preferred embodiment, this means for protecting is formed of a glass window (in particular made out of BK7 borosilicate glass) or made out of an aluminum oxide-based mineral material (in particular of sapphire) positioned at the front of the fibers.

The invention also relates to a device 1 for analyzing a sample E by spectroscopy.

As mentioned above, such a device 2 includes a spectroscopic probe 2 exhibiting the above-described features.

This analysis device 1 also includes a spectrometer incorporating the (above-mentioned) means 3 for emitting monochromatic or polychromatic light and the (above-mentioned) means 4 for measuring and/or processing at least one optical signal re-emitted by the sample E.

This analysis device 1 also includes means 5 for connecting the spectroscopic probe 2 to the spectrometer, more particularly to said means 3 for emitting monochromatic or polychromatic light and/or to said means 4 for measuring and/or processing at least one re-emitted optical signal.

In addition, this analysis device 1 includes a system 7 interposed between these connecting means 5 and said means 4 for measuring and/or processing at least one optical signal.

Such a system 7 is formed by an optical switch, an imaging device (for example a 2D CCD sensor) or (and preferably) a multiplexer.

Such a system 7 is designed so as to allow to individually measure and/or process the optical signal collected by each one of the means (24; 24') for collecting the re-emitted light.

As mentioned above, this analysis device 1 may also include an element 6, interposed between the contact surface 22 that the probe 2 includes and the sample E to be analyzed, and designed so as to diffuse at least the incident light.

In fact, such a diffusing element 6 can be either independent from the probe 2 (in particular in the form of a movable element positioned at the surface of the sample E and with respect to which the probe 2 moves), or associated to this probe 2. The probe 2 may then include means for mounting and/or receiving (notably in a removable way) such a diffusing element 6.

Such a diffusing element 6 advantageously allows illuminating this sample E in a diffuse way and over a large surface, notably over a surface the extension of which is considerably larger than that of the contact surface 22 of the probe 2.

Using such a diffusing element 6 then advantageously makes it possible to analyze very absorbent samples E (such as for example bitumen, graphite, a paint, coal ... ) or very diffusing samples E (such as for example a powder product, in particular a powder, flour ... ).

Finally, the analysis device 1 according to the invention may also include means (not shown) for positioning the sample E aligned with respect to the probe 2. In particular this probe 2 may then include such positioning means, which will be associated to this probe 2 (notably by being placed on the probe 2) through appropriated means.

In fact, such positioning means is advantageously designed so as to align the probe 2 with respect to a sample E, in particular when the sample E has a curved surface (as this is the case for a sample E formed of a pharmaceutical tablet or the like).

The present invention also relates to a method for detecting, by spectroscopy, an inhomogeneity I in a sample E.

In this respect, it should be noted that in the following description reference will be made to an inhomogeneity I that can be of a physical type (such as an aggregate, a grain, a block of material or the like) as well as of a chemical type (such as a different concentration or the like and constituting a lack of uniformity of the sample E).

This method consists in that:
the sample E is illuminated with incident light, this through means 23 for illuminating this sample E with such incident light;
the light re-emitted by the sample E under the action of the incident light is collected, this through means (24; 24') for collecting such light re-emitted by the sample E.

This method is characterized in that:
the light re-emitted by the sample E is collected, this at various spots arranged each spaced apart from the other ones and located at the same distance from the means 23 for illuminating this sample E or their barycenter;
on the basis of the signals corresponding to the light re-emitted and collected at least at two different spots, the presence of an inhomogeneity I in the sample E is determined.

According to another feature of this method, the light re-emitted by the sample E is collected, this at different spots arranged on a circle (C; C') the center of which coincides with the means 23 for illuminating the sample or with their barycenter.

These various spots are preferably regularly angularly distributed on this circle (C; C').

In addition and as mentioned above, these spots are distributed over such a circle (C; C') so that two of these spots following each other on the circle (C; C') are angularly shifted by an angle $\alpha$ between 30 and 180°, preferably between 36 and 120°.

As mentioned above, this method allows determining the presence of an inhomogeneity I in the sample E on the basis of the signals corresponding to the light re-emitted and collected at least at two different spots.

In this respect, it should be noted that, according to a first embodiment, this method allows determining the presence of a chemical inhomogeneity in the sample E, this:
by dividing a signal corresponding to the light collected at one spot by a signal corresponding to the light collected at another spot;
and by identifying, through this division, a peak (notably for a given wavelength).

According to this same embodiment, this method also allows determining the presence of a physical inhomogeneity in the sample E, this:
by dividing a signal corresponding to the light collected at one spot by a signal corresponding to the light collected at another spot;
and by identifying, through this division, a quotient different from 1.

According to a second embodiment, this method also allows determining the presence of an inhomogeneity I in the sample E, this:
by calculating a reliability interval relative to possible variations of a signal corresponding to the light re-emitted by at least one reference sample considered as homogeneous;
by identifying a signal, corresponding to the light collected on a spot of a sample E to be analyzed, and located outside this reliability interval.

Of course, this embodiment requires, previously to the calculation of the reliability interval, the analysis, by spectroscopy, of at least the reference sample considered as homogeneous.

Finally, according to a third embodiment, this method consists in that the presence of an inhomogeneity I in the sample E is determined, this:
by proceeding to a main components analysis;
by using as a statistic criterion the Hotteling distance, the residues or the levers.

Another feature consists in that this method for detecting, by spectroscopy, an inhomogeneity I in a sample E can advantageously be implemented by an analysis device 1 having the above-described features and/or including at least one spectroscopic probe 2 having the above-described features.

In particular and as mentioned above, this method consists in that the light re-emitted by the sample E is collected, this at different spots located at the same distance d from the means 23 for illuminating this sample E or their barycenter.

In fact, for collecting the light re-emitted by the sample E at these different spots of this sample E, it is particularly advantageous to use the spectroscopic probe 2 object of the present invention and including, as described above, means (24; 24') for collecting the light re-emitted by the sample forming at least one set (25; 25') of means (24; 24') for collecting this re-emitted light. Such a set (25; 25') includes, as mentioned above, a plurality of these means (24; 24') for collecting the re-emitted light arranged each spaced apart from the other ones and at the same distance (d; d') from the means 23 for illuminating the sample E or their barycenter. These means (24; 24') that such a set (25; 25') includes are thus positioned at different spots located at the same distance (d; d') from the means 23 for illuminating this sample E or their barycenter, which therefore makes it possible to implement the method according to the invention.

Such a probe 2 may then include one single set 25 of means 24 for collecting this re-emitted light. These means 24 are arranged on the probe 2 (in particular at the level of the contact surface 22 of this probe 2), on different spots located at the same distance d from the means 23 for illuminating this sample E or their barycenter. Thus, the method according to the invention consists in collecting the light re-emitted by the sample E at different spots of this sample E corresponding to the position of the means 24 for collecting the re-emitted light, which this single set 25 of means 24 includes.

However and as described above, such a probe 2 may also include a plurality of sets (25; 25') of means (24; 24') for collecting the light re-emitted by the sample E.

In such a case, the method for detecting, by spectroscopy, an inhomogeneity I is ensured by implementing such a probe 2 and, in particular, by proceeding to a detection of an inhomogeneity I by implementing one of these sets (25; 25') or a plurality of these sets (25; 25'), this individually and for each one of these sets (25; 25').

In fact, by implementing a plurality of these sets (25; 25'), the method consists in that the light re-emitted by the sample E is collected at different spots located at the same distance (d; d') from the means 23 for illuminating this sample E or their barycenter and corresponding to a same set (25; 25') of means (24; 24'), this for each one of the sets (25; 25') of the plurality of sets (25; 25') implemented.

The invention then also relates to the use of a spectroscopic probe 2 exhibiting the above-described features (and which can be developed and designed specifically), for implementing this method for detecting, by spectroscopy, an inhomogeneity I in a sample E.

However, this method for detecting, by spectroscopy, an inhomogeneity I in a sample E can also be implemented by means of a spectroscopic probe other than the one object of the present invention.

Such a spectroscopic probe may then include means (in particular formed of an optical fiber or a bundle of optical fibers) for illuminating such a sample E, as well as means for collecting the light re-emitted by this sample E and formed of a bundle of optical fibers arranged around the means for illuminating the sample, notably on a circle and/or jointed.

The method then consists in measuring and processing the optical signal collected by the fibers or groups of fibers arranged at the same distance from the illuminating means and spaced each apart from the other ones, in particular as described above (angular distribution, angular shifting, separation ... ).

The present invention also relates to a method for determining, by spectroscopy, the absorption coefficient μa and/or the diffusion coefficient μs' of a sample E.

This method consists in that:
the sample E is illuminated with incident light, this through means 23 for illuminating this sample E with such incident light;
the light re-emitted by the sample under the action of the incident light is collected, this through means (24; 24') for collecting such light re-emitted by the sample E;

This method is characterized in that:
the light re-emitted by the sample E is collected, this at least at two different spots, each located at a different distance (d; d') from the means 23 for illuminating this sample or their barycenter;
on the basis of the signals corresponding to the light re-emitted and collected at these different spots, the absorption coefficient μa and/or the diffusion coefficient μs' of the sample E are determined.

In fact, this method consists in that, when the light re-emitted by the sample E is collected, this light is collected at least at one spot located on a first circle C the center of which coincides with the means 23 for illuminating the sample or their barycenter, as well as at least on another spot located on a second circle C', the radius of which is different from that of the first circle C and the center of which coincides with the means for illuminating the sample or their barycenter.

In this respect, it should be noted that the method for determining, by spectroscopy, the absorption coefficient μa and/or the diffusion coefficient μs' of a sample E can advantageously be implemented through a spectroscopic probe 2 (as described above) including a plurality of sets (25; 25') of means (24; 24') for collecting the light re-emitted by a sample E and/or by an analysis device 1 including at least such a spectroscopic probe 2.

Here too, the light collected on a spot located at a distance (d; d') from the means 23 for illuminating the sample E or their barycenter is collected by means (24; 24') for collecting such light, which a set (25; 25') of these means (24; 24') includes.

As mentioned above, the method according to the invention consists in that the absorption coefficient μa and/or the diffusion coefficient μs' of the sample E is determined on the basis of the signals corresponding to the light re-emitted by the sample E and collected on different spots of this sample E.

In fact and according to another feature of this method, in order to determine these absorption coefficient μa and/or diffusion coefficient μs', these signals are analyzed using the equation of diffusion of Farrel, this within the framework of the spatially resolved spectroscopy technique.

In this respect, it should be noted that the signals corresponding to the light re-emitted by the sample E and collected at different spots of this sample E are in the form of a spectrum, which takes into consideration the absorption coefficient μa and/or the diffusion coefficient μs' and which constitutes, in fact, a combination of these coefficients (μa and μs'). This combination is characterized by a simplified analytical equation:

$$R(\rho) = I_0 z_0 \frac{\exp(-\mu_{\text{eff}} \rho)}{2\pi \rho^2}\left(\mu_{\text{eff}} + \frac{1}{\rho}\right) \quad (1)$$
$$= I_0 z_0 f(\mu_{\text{eff}}, \rho)$$

wherein z0=1/μs', I0 is the intensity of the light source in the medium, ρ is the distance with respect to the radiation source and μeff is a non-linear combination of μa and μs':

$$\mu_{\text{eff}} = \sqrt{3\mu_a(\mu_a + \mu_s')} \quad (2)$$

In addition, the spectrum, obtained by spectroscopy by implementing this method, also reads as follows:

$$R(\rho) = \frac{I_0 a}{4\pi} \left[ \frac{1}{\mu_{tr}} \left( \mu_{eff} \frac{1}{r_1} \right) \frac{\exp(-\mu_{eff} r_1)}{r_1^2} + \left( \frac{1}{\mu_{tr}} + 2z_b \right) \left( \mu_{eff} + \frac{1}{r_2} \right) \frac{\exp(-\mu_{eff} r_2)}{r_2^2} \right] \quad (3)$$

wherein:
$\mu_{eff} = [3\mu_a(\mu_a+\mu_s')]^{-1}$
$a = \mu_s'/\mu_{tr}$
$r_1 = [z_0^2 + \rho^2]^{1/2}$
$r_2 = [(z_0+2z_b)^2 + \rho^2]^{1/2}$
$z_0 = 1/\mu_s'$
$z_b = 2AD$ Wherein:
D is the diffusion coefficient (depending on μa and μs');
A is a parameter which is invariable during a same measurement, and which allows taking into consideration the refractive index difference at the surface of the medium.

Therefore, when determining the absorption coefficient μa and/or the diffusion coefficient μs' of the sample E, this according to the method of the invention, the above equation systems are, in fact, resolved.

Finally, when proceeding, by spectroscopy and by implementing a method described above, to the detection of an inhomogeneity I and/or to the determination of the absorption coefficient and/or the diffusion coefficient of a sample E, this sample E is brought into contact either directly with the probe 2 (in particular with the contact surface 22 of the probe 2), or with the diffusing element 6, which is then interposed between this sample E and the probe 2 (more particularly the contact surface 22 of the probe 2).

Irrespective of the nature of this contact, this sample E is positioned at a distance from the probe 2 (more particularly from the contact surface 22 of the latter 2) smaller than 5 cm.

What is claimed:

1. Spectroscopic probe (2) for a device for analyzing (1) a sample (E) by spectroscopy, including:
    means (23) for illuminating the sample (E) to be analyzed with incident light;
    means (24; 24') for collecting light re-emitted by the sample (E) under the action of the incident light;
    a contact surface (22) oriented towards the sample (E), at the level of which, or nearby which the means (23) for illuminating the sample and/or the means (24; 24') for collecting the re-emitted light are located;
    wherein:
    the means (24; 24') for collecting the light re-emitted by the sample (E) constitute at least one set (25; 25') of said means (24; 24') for collecting the re-emitted light;
    such a set (25; 25') including a plurality of these means (24a, 24b, 24c; 24'a, 24'b, 24'c) for collecting the re-emitted light;
    each means of the plurality of these means (24a, 24b, 24c; 24'a, 24'b, 24'c) for collecting the re-emitted light being spaced apart from each other and at the same distance from the means (23) for illuminating the sample (E) or their barycenter;
    each means of the plurality of these means (24a, 24b, 24c; 24'a, 24'b, 24'c) for collecting the re-emitted light including one series (241; 241') of optical fibers (240; 240') formed of a plurality of optical fibers (240; 240') which are juxtaposed.

2. Spectroscopic probe (2) according to claim 1, wherein:
    the means (24; 24') for collecting the light re-emitted by the sample (E) constitute a plurality of sets (25; 25') of means (24; 24') for collecting the re-emitted light;
    each of these sets (25; 25') including a plurality of these means (24a, 24b, 24c; 24'a, 24'b, 24'c) for collecting the re-emitted light arranged each spaced apart from the other ones and at the same distance from the means (23) for illuminating the sample (E) or their barycenter;
    the means (24; 24') for collecting the re-emitted light which such a set (25; 25') includes being located, with respect to the means (23) for illuminating the sample (E) or their barycenter, at a distance (d; d') differing from the distance (d'; d) at which are located the means (24'; 24) for collecting the re-emitted light which another set (25'; 25) includes.

3. Spectroscopic probe (2) according to claim 1, wherein the means (24; 24') for collecting the light re-emitted by the sample (E) which a same set (25; 25') of these means (24; 24') includes, are arranged on a circle (C; C') the center of which coincides with the means (23) for illuminating the sample (E) or their barycenter.

4. Spectroscopic probe according to claim 3, wherein the means (24; 24') for collecting the light re-emitted by the sample (E) which a same set (25; 25') of these means (24; 24') includes, are regularly angularly distributed over the circle (C; C').

5. Spectroscopic probe (2) according to claim 3, wherein the means (24; 24') for collecting the light re-emitted by the sample (E) which a same set (25; 25') of these means (24; 24') includes, are distributed over the circle (C; C') so that two means (24; 24') for collecting the re-emitted light following each other on this circle (C; C') are angularly shifted by an angle (α) comprised between 30 and 180°.

6. Spectroscopic probe (2) according to claim 1, wherein the one series (241; 241') of optical fibers includes 3 optical fibers (240; 240').

7. Spectroscopic probe (2) according to claim 1, wherein the optical fibers (240; 240') constituting one series (241; 241') of optical fibers (240; 240') are arranged according to an arc of circle the center of which coincides with the means (23) for illuminating the sample or their barycenter.

8. Spectroscopic probe (2) according to claim 1, wherein the means (23) for illuminating the sample (E) include at least one optical fiber (230) or at least one bundle (231) of optical fibers (230).

9. Spectroscopic probe (2) according to claim 6, wherein an optical fiber (240, 240', 230) has an end positioned either at the level of the contact surface (22) of the probe (2), flush with this contact surface (22), or nearby this contact surface (22), set back with respect to this contact surface (22).

10. Spectroscopic probe (2) according to claim 1, wherein the contact surface (22) of the probe (2) includes at least one means (220) for receiving the light re-emitted by the sample (E), this means (220) being of a reflecting type and being formed, either of at least one polished or white portion of this contact surface (22), or of a reflecting coating that at least one portion of this contact surface (22) includes.

11. Spectroscopic probe (2) according to claim 1, wherein the contact surface (22) of the probe (2) includes at least one means (220) for receiving the light re-emitted by the sample (E), this means (220) being of an at least partially absorbent type and being formed, either of a colored material forming at least one portion of this contact surface (22), or of a colored coating that at least one portion of this contact surface (22) includes.

12. Spectroscopic probe (2) according to claim 1, wherein the probe (2) includes one means for protecting the means (23) for illuminating the sample and/or the means (24; 24') for collecting light re-emitted by the sample (E) and/or the contact surface (22), such means for protecting being positioned at the front and against the contact surface (22).

13. Device for analyzing (1) a sample (E) by spectroscopy, including:
   a spectroscopic probe (2) according to claim 1;
   a spectrometer incorporating means (3) for emitting monochromatic or polychromatic light, and means (4) for measuring and/or processing at least one optical signal re-emitted by the sample (E);
   means (5) for connecting the probe (2) to the spectrometer, and a multiplexer (7) interposed between said means (5) for connecting the probe (2) to the spectrometer and said means (4) for measuring and/or processing at least one optical signal.

14. Device for analyzing (1) according to claim 13, wherein the device includes an element (6), interposed between the contact surface (22) which the probe (2) includes and the sample (E) to be analyzed, and designed so as to diffuse at least the incident light.

15. Method for detecting, by spectroscopy, an inhomogeneity (I) in a sample (E), this method consisting in that:
   the sample (E) is illuminated with incident light, using means (23) for illuminating the sample (E) with incident light;
   the light re-emitted by the sample (E) is collected, using means (24; 24') for collecting the light re-emitted by the sample (E);
   wherein:
   the light re-emitted by the sample (E) is individually collected at different spots, each spot spaced apart from each other and located at the same distance from the means (23) for illuminating this sample (E) or their barycenter;
   on the basis of the signals corresponding to said light re-emitted and individually collected and processed at least at two different spots, the presence of an inhomogeneity (I) in the sample (E) is determined.

16. Method for detecting, by spectroscopy, an inhomogeneity (I) in a sample (E), according to claim 15, wherein the light re-emitted by the sample (E) is collected at different spots arranged on a circle (C; C') the center of which coincides with the means (23) for illuminating the sample (E) or their barycenter.

17. Method for detecting, by spectroscopy, a physical inhomogeneity (I) in a sample (E), according to claim 15, wherein the presence of said physical inhomogeneity (I) in the sample (E) is determined:
   by dividing a signal corresponding to the light collected at one spot by a signal corresponding to the light collected at another spot;
   and by identifying, through this division, a quotient different from 1 representative of a physical inhomogeneity (I).

18. Method for detecting, by spectroscopy, an inhomogeneity (I) in a sample (E), according to claim 15, wherein this method is implemented with a device for analyzing (1) a sample (E) by spectroscopy, including:
   a spectroscopic probe (2) for a device for analyzing (1) a sample (E) by spectroscopy, including: means (23) for illuminating the sample (E) to be analyzed with incident light; means (24; 24') for collecting light re-emitted by the sample (E) under the action of the incident light; a contact surface (22) oriented towards the sample (E), at the level of which, or nearby which the means (23) for illuminating the sample and/or the means (24; 24') for collecting the re-emitted light are located; wherein: the means (24; 24) for collecting the light re-emitted by the sample (E) constitute at least one set (25; 25') of said means (24; 24') for collecting the re-emitted light; such a set (25; 25') including a plurality of these means (24a, 24b, 24c; 24'a, 24'b, 24'c) for collecting the re-emitted light; each means of the plurality of these means (24a, 24b, 24c; 24'a, 24'b, 24'c) for collecting the re-emitted light being spaced apart from each other and at the same distance from the means (23) for illuminating the sample (E) or their barycenter; each means of the plurality of these means (24a, 24b, 24c; 24'a, 24'b, 24'c) for collecting the re-emitted light including one series (241; 241') of optical fibers (240; 240') formed of a plurality of optical fibers (240; 240') which are juxtaposed;
   a spectrometer incorporating means (3) for emitting monochromatic or polychromatic light, and means (4) for measuring and/or processing at least one optical signal re-emitted by the sample (E);
   means (5) for connecting the probe (2) to the spectrometer, and a multiplexer (7) interposed between said means (5) for connecting the probe (2) to the spectrometer and said means (4) for measuring and/or processing at least one optical signal.

19. Method for analyzing a sample by spectroscopy, comprising a method for detecting, by spectroscopy, an inhomogeneity (I) in a sample (E) according to claim 15, and a method for determining, by spectroscopy, the absorption coefficient ($\mu a$) and/or the diffusion coefficient ($\mu s'$) of a sample (E), this method for determining the absorption coefficient and/or the diffusion coefficient consisting in that:
   the light re-emitted by the sample (E) is collected at least at two different spots, each spot being located at a different distance (d; d') from the means (23) for illuminating this sample (E) or their barycenter;
   on the basis of the signals corresponding to the light re-emitted and collected at these different spots, the absorption coefficient ($\mu a$) and/or the diffusion coefficient ($\mu s'$) of the sample (E) are determined.

20. Method for determining, by spectroscopy, the absorption coefficient ($\mu a$) and/or the diffusion coefficient ($\mu s'$) of a sample (E), according to claim 19, wherein the light re-emitted by the sample (E) is collected at least at one spot on a first circle (C) the center of which coincides with the means (23) for illuminating the sample (E) or their barycenter, and at least at another spot located on a second circle (C') the radius of which differs from that of the first circle (C) and the center of which coincides with the means (23) for illuminating the sample (E) or their barycenter;
   using the signals corresponding to the light re-emitted and collected at these different spots, the absorption coefficient ($\mu a$) and/or the diffusion coefficient ($\mu s'$) of the sample (E) are determined.

21. Spectroscopic probe (2) according to claim 3, wherein the means (24; 24') for collecting the re-emitted light that one set (25; 25') of these means (24; 24') includes are located on the bisecting line of an angle formed, respectively, by two successive means (24'a, 24'b; 24a, 24b) for collecting the re-emitted light that another set (25'; 25) of these means (24'; 24) includes, and by the illuminating means (23) or their barycenter.

22. Method for detecting, by spectroscopy, a chemical inhomogeneity (I) in a sample (E), according to claim 15, wherein the presence of said chemical inhomogeneity (I) in the sample (E) is determined:
   by dividing a signal corresponding to the light collected at one spot by a signal corresponding to the light collected at another spot;
   and by identifying, through this division, a peak at least for a given wavelength representative of a chemical inhomogeneity (I).

23. Method for detecting, by spectroscopy, an inhomogeneity (I) in a sample (E), according to claim 15, wherein the presence of said inhomogeneity (I) in the sample (E) is determined:
   by calculating a reliability interval relative to possible variations of a signal corresponding to the light re-emitted by at least one reference sample considered as homogeneous;
   by identifying a signal, corresponding to the light collected on a spot of a sample E to be analyzed, and located outside this reliability interval.

* * * * *